(12) United States Patent
Fellous et al.

(10) Patent No.: US 9,133,242 B2
(45) Date of Patent: Sep. 15, 2015

(54) PEPTIDE FOR USE AS A MEDICAMENT, IN PARTICULAR FOR THE TREATMENT OF CANCER

(76) Inventors: Esther Suzy Arlette Fellous, Paris (FR); Jorge Kalil, Sao Paulo SP (BR); Mario Palma, Rio Claro SP (BR)

( * ) Notice: Subject to any disclaimer, the term of this patent is extended or adjusted under 35 U.S.C. 154(b) by 79 days.

(21) Appl. No.: 13/698,196

(22) PCT Filed: May 20, 2011

(86) PCT No.: PCT/FR2011/051150
§ 371 (c)(1),
(2), (4) Date: May 16, 2013

(87) PCT Pub. No.: WO2011/148083
PCT Pub. Date: Dec. 1, 2011

(65) Prior Publication Data
US 2013/0230591 A1    Sep. 5, 2013

(30) Foreign Application Priority Data

May 27, 2010    (FR) ..................................... 10 54106

(51) Int. Cl.
*C07K 7/08*    (2006.01)
*C07K 7/06*    (2006.01)
*A61K 38/00*   (2006.01)

(52) U.S. Cl.
CPC ... *C07K 7/08* (2013.01); *C07K 7/06* (2013.01); *A61K 38/00* (2013.01)

(58) Field of Classification Search
CPC ............. C07K 7/08; C07K 7/06; A61K 38/00
See application file for complete search history.

(56) References Cited

FOREIGN PATENT DOCUMENTS

WO    00/02581 A1    1/2000

OTHER PUBLICATIONS de Souza et al., 2008, Monitoring the positioning of short polycationic peptides in model lipid bilayers by combining hydrogen/deuterium exchange and electrospray ionization mass spectrometry, Biochimica et Biophysica Acta, 1778: 2797-2805.*
Lokeshwar et al., 2008, Seminars in Cancer Biology, 18: 281-287.*
Huang et al., 2001, Current Opinion in Genetics & Development, 11: 104-110.*
Antolin-Amerigo et al., 2014, Curr Allergy Asthma Rep, 14: 449-460.*
Thermo Electron Corporation, 2004, N-terminal Acetylation and C-terminal Amidation of Peptides, 2 pages.*
Liu et al., 1994, Peptide segment ligation strategy without use of protecting groups, PNAS, 91: 6584-6588.*
Albericio, 2004, Developments in peptide and amide synthesis, Current Opinion in Chemical Biology, 8: 211-221.*
Liberio et al., 2013, Anticancer Peptides and proteins: A Panoramic View, Protein & Peptide Letters, 20: 380-391.*
De Souza Bibiana Monson et al. : "Monitoring the positioning of short polycationic peptides in model lipid bilayers by combining hydrogen/deuterium exchange and electrospray ionization mass spectrometry", Biochimica Et Biophysica Acta, vol. 1778, No. 12, Sep. 25, 2008, pp. 2797-2805, XP025658338, ISSN: 0005-2736, DOI: 10.1016/j.bbamem.2008.09.005 abstract; figure 3 p. 2798, right-hand column, paragraph 2.1, Cited in ISR.
International Search Report, dated Oct. 20, 2011, from corresponding PCT application, 4 pages.

* cited by examiner

*Primary Examiner* — Amber D Steele
(74) *Attorney, Agent, or Firm* — Young & Thompson

(57) ABSTRACT

The invention relates to a peptide having the sequence SEQ.1: INWLKIAKKVAGML-NH2 and one or more of the variants thereof selected from among the sequences SEQ.2 to SEQ.25, or one of the mixtures thereof. The peptides are used especially as a medicament, in particular for the treatment of cancer. The invention also relates to a pharmaceutical composition including the peptides.

16 Claims, 7 Drawing Sheets

PEPTIDE FOR USE AS A MEDICAMENT, IN PARTICULAR FOR THE TREATMENT OF CANCER

The present invention relates to a pharmaceutical composition comprising at least one particular peptide, for use thereof as a medicament in the treatment of cancer.

For treating cancer, three types of therapies conventionally exist: surgery which aims to remove the tumor, radiotherapy which aims to destroy the tumor via rays, and medical treatments (chemotherapy). Surgery and radiotherapy are extensive treatments which are difficult for the patient to endure. In addition, these three treatments must usually be combined, since they are complementary. They must be combined in the context of a programmed strategy.

With regard to the medical treatments, their objective is to treat not only the organ affected, but also the entire body through the administration of anticancer medicaments. Thus, unlike surgery or radiotherapy, which treat the tumor only locally, only medical treatments have a systemic action which makes it possible to treat a tumor that has already disseminated or that is in the process of doing so. Several types of medical treatments exist: cytotoxic chemotherapy and hormone therapy are the most conventional; immunotherapy, gene therapy and non-cytotoxic therapies are still within the sphere of research.

Document WO 00/02581 relates to the use of a peptide for producing a medicament intended for the treatment or prophylaxis of cancer, the peptide consisting in particular of the sequences EARPALLTSRLRFIPK (SEQ ID NO: 26), DGL-RPIVNMDYVVGAR (SEQ ID NO: 27), GVPEYGCVVN-LRKTVVNF (SEQ ID NO: 28), ILAKFLHVVL (SEQ ID NO: 29) or ELLRSFFYV (SEQ ID NO: 30).

The publication "Monitoring the positioning of short polycationic peptides in model lipid bilayers by combining hydrogen/deuterium exchange and electrospray ionization mass spectrometry" by Bibiana Monson de Souza and Mario Sergio Palma, from Biochimica et Biophysica Acta, 2008, pages 2797 to 2805, describes the use of electrospray ionization mass spectrometry for analyzing the hydrogen/deuterium exchange properties of the Apoica-MP INWLKI-AKKVAGML-$NH_2$ (SEQ ID NO: 1) peptide.

Despite thorough research in this field, there is not yet at the current time a medicament which both is effective in the treatment of cancers and preserves the healthy cells of a human or animal body. Current chemotherapy always causes side effects with a greater or lesser degree of seriousness.

The objective of the present invention is to propose a novel peptide medicament and a novel pharmaceutical composition which avoid all or some of these side effects.

To this effect, the subject of the invention is a peptide comprising at least one sequence chosen from: the sequences SEQ. 2 to SEQ. 25.

The invention also relates to a peptide comprising at least one sequence chosen from: the sequences SEQ. 1 to SEQ. 25 for use as a medicament.

Preferably, the peptides of sequences SEQ. 1 to SEQ. 25 are used in the treatment of cancer.

In particular, the sequences of the peptides which act as an active ingredient for treating cancer are the following (table I):

TABLE I

| SEQ sequence number (EZ code) | Sequences | Number of amino acids |
|---|---|---|
| 1 (EZ 6) | INWLKIAKKVAGML-$NH_2$, i.e.<br>Ile Asn Trp Leu Lys Ile Ala Lys Lys Val Ala Gly Met Leu-$NH_2$ | 14 |
| 2 (EZ 7) | INWLKIAKKVAGML, i.e.<br>Ile Asn Trp Leu Lys Ile Ala Lys Lys Val Ala Gly Met Leu | 14 |
| 3 (EZ 8) | INWLAIAKKVAGML-$NH_2$, i.e.<br>Ile Asn Trp Leu Ala Ile Ala Lys Lys Val Ala Gly Met Leu-NH2 | 14 |
| 4 (EZ 9) | INWLAIAAKVAGML-$NH_2$, i.e.<br>Ile Asn Trp Leu Ala Ile Ala Ala Lys Val Ala Gly Met Leu-NH2 | 14 |
| 5 (EZ 10) | INWLKIAAAVAGML-$NH_2$, i.e.<br>Ile Asn Trp Leu Lys Ile Ala Ala Ala Val Ala Gly Met Leu-NH2 | 14 |
| 6 (EZ 11) | INWLAIAAAVAGML-$NH_2$, i.e.<br>Ile Asn Trp Leu Ala Ile Ala Ala Ala Val Ala Gly Met Leu-NH2 | 14 |
| 7 (EZ 12) | INWKKIAKKVAGML-$NH_2$, i.e.<br>Ile Asn Trp Lys Lys Ile Ala Lys Lys Val Ala Gly Met Leu-NH2 | 14 |
| 8 (EZ 13) | INWLKIKKKVAGML-$NH_2$, i.e.<br>Ile Asn Trp Leu Lys Ile Lys Lys Lys Val Ala Gly Met Leu-NH2 | 14 |
| 9 (EZ 14) | INWLKIAKKVKGML-$NH_2$, i.e.<br>Ile Asn Trp Leu Lys Ile Ala Lys Lys Val Lys Gly Met Leu-NH2 | 14 |

TABLE I-continued

| SEQ sequence number (EZ code) | Sequences | Number of amino acids |
|---|---|---|
| 10 (EZ 15) | INWKKIKKKVAGML-NH$_2$, i.e.<br>Ile Asn Trp Lys Lys Ile Lys Lys Lys Val Ala Gly Met Leu-NH2 | 14 |
| 11 (EZ 16) | INWKKIKKKVKGML-NH$_2$, i.e.<br>Ile Asn Trp Lys Lys Ile Lys Lys Lys Val Lys Gly Met Leu-NH2 | 14 |
| 12 (EZ 17) | LKIAKKVAGML-NH$_2$, i.e.<br>Leu Lys Ile Ala Lys Lys Val Ala Gly Met Leu-NH2 | 11 |
| 13 (EZ 18) | LKIAKKVAGML, i.e.<br>Leu Lys Ile Ala Lys Lys Val Ala Gly Met Leu | 11 |
| 14 (EZ 19) | KIAKKVAGML-NH$_2$, i.e.<br>Lys Ile Ala Lys Lys Val Ala Gly Met Leu-NH2 | 10 |
| 15 (EZ 20) | KIAKKVAGML, i.e.<br>Lys Ile Ala Lys Lys Val Ala Gly Met Leu | 10 |
| 16 (EZ 1) | Biotin-INWLKIAKKVAGML-NH$_2$, i.e.<br>Biotin-Ile Asn Trp Leu Lys Ile Ala Lys Lys Val Ala Gly Met Leu-NH2 | 14 |
| 17 (EZ 2) | FITC-INWLKIAKKVAGML-NH$_2$, i.e.<br>Phe Ile Thr Cys Ile Asn Trp Leu Lys Ile Ala Lys Lys Val Ala Gly-NH2 | 14 |
| 18 (EZ 3) | INWLKIAKKVAGM-NH$_2$, i.e.<br>Ile Asn Trp Leu Lys Ile Ala Lys Lys Val Ala Gly Met-NH2 | 13 |
| 19 (EZ 4) | INWLKIAKKVAG-NH$_2$, i.e.<br>Ile Asn Trp Leu Lys Ile Ala Lys Lys Val Ala Gly-NH2 | 12 |
| 20 (EZ 5) | INWLKIAKKVA-NH$_2$, i.e.<br>Ile Asn Trp Leu Lys Ile Ala Lys Lys Val Ala-NH2 | 11 |
| 21 (EZ 21) | INALKIAKKVAGML-NH$_2$, i.e.<br>Ile Asn Ala Leu Lys Ile Ala Lys Lys Val Ala Gly Met Leu-NH2 | 14 |
| 22 (EZ 22) | INALKIAKKVAGML, i.e.<br>Ile Asn Ala Leu Lys Ile Ala Lys Lys Val Ala Gly Met Leu | 14 |
| 23 (EZ 23) | INKLKIAKKVAGML-NH$_2$, i.e.<br>Ile Asn Lys Leu Lys Ile Ala Lys Lys Val Ala Gly Met Leu-NH2 | 14 |
| 24 (EZ 24) | INKLKIAKKVAGML, i.e.<br>Ile Asn Lys Leu Lys Ile Ala Lys Lys Val Ala Gly Met Leu | 14 |
| 25 (EZ 25) | KLKIAKKVAGML-NH$_2$, i.e.<br>Lys Leu Lys Ile Ala Lys Lys Val Ala Gly Met Leu-NH2 | 12 |

The studies by the applicant on these peptides of SEQ. 1 to SEQ. 25 have made it possible to demonstrate, surprisingly, that these peptides have a cytotoxic activity against cancer cells while at the same time being very weakly toxic or not toxic for the cells of the host to be treated. The active peptides according to the invention in fact specifically modify the microtubules of cancer cells.

Microtubules, which are constituents of one of the three filament networks of the cytoskeleton, are complex, unstable polymers, the base unit of which is the α- and β-tubulin dimer. They are responsible for many cell movements, axonal transport, or motility, for example, and they especially provide the base material for forming the mitotic spindle. Microtubules are perpetually reforming hollow tubes of variable length. Thus, by disrupting the dynamics of the microtubules of cancer cells, the peptides according to the invention also act as antimitotic agents preventing the proliferation of cancer cells (slowing down or arresting cancer cell mitosis).

The active peptides according to the invention also appear to specifically modify the plasma membranes of cancer cells and do not appear to induce these same modifications in the healthy cells of the host organism. This would be explained by the fact that the active peptides, because of their polycationic nature, would act on the plasma membranes of cancer cells rich in negative charges.

Consequently, the active peptides according to the invention have an action on two different cell compartments: the intracellular cytoskeleton and the plasma membrane of cancer cells.

The active peptides, which comprise only 10 to 14 amino acids, also have the advantage of being very easy to synthesize.

Preferably, the peptide(s) cited in table I, applied for use as a medicament for treating cancer, are in particular effective for treating breast cancer, glioblastoma, brain, cervical, colorectal, cutaneous, endometrial, stomach, liver, and gastrointestinal stromal cancer, malignant hemopathies (leukemia, multiple myeloma, lymphomas (Hodgkin's disease, non-Hodgkin's lymphoma), hepatocellular carcinoma, Kaposi's sarcoma, cancer of the larynx, mesothelioma, esophageal cancer, eye cancer, osteosarcoma, ovarian cancer, pancreatic cancer, skin (in particular mouth) cancer, lung cancer, prostate cancer, rhabdomyosarcoma, kidney, breast, testicular and thyroid cancer, soft tissue cancer, bladder carcinoma, myeloma (bone cancer) and plasmocytoma.

According to another characteristic of the invention, the peptides of sequences SEQ. 1 to SEQ. 25 are produced by chemical synthesis.

Another objective of the present invention concerns a pharmaceutical composition comprising one of the peptides as defined above.

Advantageously, the composition is in the form of an aqueous suspension or solution, or in the dry state in the form of uncoated or coated tablets, such as pills, gel capsules, capsules or powders.

If the pharmaceutical composition is in the dry state, it can be mixed with one or more inert diluents, such as starch, cellulose, succrose, lactose or silica, etc. It can also comprise other substances in the dry state, for instance one or more lubricants, such as magnesium stearate or talc, a colorant, a coating (sugar-coated tablets) or a varnish.

If the pharmaceutical composition according to the invention is in liquid form, it can comprise pharmaceutically acceptable solutions, suspensions, emulsions, syrups and elixirs containing inert diluents such as water, ethanol, glycerol, vegetable oils or liquid paraffin. The pharmaceutical composition can comprise other liquid substances other than the diluents, for example wetting, sweetening, thickening, flavoring or stabilizing products.

Preferably, the composition, optionally combined with a pharmaceutically acceptable, nontoxic, inert excipient or vehicle, is characterized in that it can be administered topically in the form of a cutaneous, transcutaneous or percutaneous; oral; parenteral; nasal or bronchial application.

The pharmaceutical composition for parenteral administration can preferably be an aqueous or nonaqueous solution, a suspension or an emulsion. As solvent or vehicle, mention will be made of water, propylene glycol, vegetable oils, in particular olive oil or sesame oil, injectable organic esters, for example ethyl oleate, or other suitable organic solvents. The pharmaceutical composition can also contain adjuvants, in particular wetting, isotonizing, emulsifying, dispersing and stabilizing agents.

For topical administration, the medicaments will advantageously be administered in the form of ointments, creams, gels or patches.

In particular, the pharmaceutical composition is sterile.

The sterilization can be carried out in several ways, for example by aseptic filtration, by incorporating sterilizing agents into the composition, by irradiation or by heating. The medicaments can also be prepared in the form of sterile solid compositions which can be dissolved at the time of use in sterile water or any other injectable sterile medium.

The pharmaceutical composition may in addition be used alone or in combination, in a given treatment with other medicaments, or combined with radiotherapy or surgery.

The invention will be understood more clearly, and other objectives, details, characteristics and advantages thereof will appear more clearly, during the following description of one particular embodiment of the invention, given purely by way of nonlimiting illustration, with reference to the appended drawings. Examples of the pharmaceutical assays are also provided for the purposes of illustration, but they can in no way be interpreted as limiting the scope of the invention.

In these drawings:

FIG. 1 represents the effect of the peptide of SEQ. 1 on the polymerization of microtubules of a healthy rat brain at doses of 23.3 µM, 46.6 µM, 70 µM and 93.3 µM, and also the effect of a control sample which was not subjected to the peptide of SEQ. 1; in particular, FIG. 1 represents the change in the in vitro polymerization of rat brain microtubules, quantified by measurements of optical density at a wavelength of 345 nm, as a function of time in minutes and in the presence or absence of peptide of SEQ. 1;

FIG. 2 represents the effect of the peptide of SEQ. 1 at the doses of 46.6 µM, 70 µM, 93.3 µM and 116 µM on the stability of the microtubules of a healthy rat brain, evaluated by the percentage of microtubule depolymerization induced by a treatment of 30 min at 4° C. of the microtubules assembled beforehand at 37° C. for 15 min;

FIG. 3 represents photos of the A549 cell line (lung cancer) treated with the peptide of SEQ. 1 at 15 µM and not treated with this peptide (control at 0 µM), of the NMT-1 cell line treated with the peptide of SEQ. 1 at 15 µM and not treated with this peptide (control) and of the PANC-1 cell line (pancreatic cancer) treated with the peptide of SEQ. 1 at 15 µM and not treated with this peptide (control);

FIG. 4 represents photos of non-tumor cell lines, FIBRO 1 and FIBRO 2 (fibroblast cells), treated with the peptide of SEQ. 1 at 15 µM and not treated with this peptide (control);

FIG. 5 represents four graphs representing the viability of the cells of various lines: T (Cos kidney line); G (A549 lung line); C (HepG2 liver line); R (PANC1 pancreatic line); S (MiaPaCa pancreatic line); X (H2 95 R adrenal line); Y (MNT-1 melanoma line); leukemic lymphocyte lines L1 (HL 60); L3 (U 937); L4 (NB 4); L5 (MenoMac6), and a normal lymphocyte line L6, as a function of the concentration of the peptide of SEQ. 1;

FIG. 6 represents four phase contrast images of A 549 cancer cells (lung cancer) showing their morphology in the absence of the peptide of SEQ. 1 (control images A and B) and the modifications to their morphology induced by 15 µM of the peptide of SEQ. 1 (image C taken 4 hours after the injection of the peptide of SEQ. 1 and image D taken 2 h after the injection of the peptide of SEQ. 1); and FIG. 7 is a graph showing the effect of the peptide of SEQ. 1 (concentration of 15 µM) on the loss of substrate-adhesiveness of A 549 cancer cells as a function of time.

A) MATERIALS AND METHODS

A1) Synthesis of the Peptides SEQ. 1 to SEQ. 25 and Purification

The peptides are prepared by manually fractionated solid-phase synthesis using N-9-fluorophenylmethoxycarbonyl with a Novasyn TGS resin. The side chains protect the groups including t-butyl for serine and t-butoxycarbonyl for lysine. In order to prepare the peptides having an acetylated N-terminal residue, after the coupling of the final amino acid residue, acetic anhydride was added to the resin-peptide complexes and kept stirring for 1 hour in order to promote acetylation.

The resin-peptide complexes were cleaved by treatment with trifluoroacetic acid/1,2-ethanedithiol/anisole/phenol/water (82.5:2.5:5:5:5 by volume) at a concentration of 10 mL·g$^{-1}$ at ambient temperature for 2 hours. Filtration was subsequently carried out in order to remove the resin. Ethyl ether at 4° C. was then added, causing precipitation of the crude peptides which were subsequently collected after centrifugation at 1000 g for 15 minutes at ambient temperature. The crude peptides were subsequently solubilized in water and chromatographed by RP-HPLC using a Shiseido C-18 semi-preparative column (250 mm×10.0 mm; 5 µm) under isocratic elution with 40% (v/v) of acetonitrile containing 0.1% (v/v) of TFA at a rate of 2 mL/min. The elution was regulated at 215 nm with a UV-DAD detector (ultraviolet-diode array detector) (Shimadzu, model SPD-M10A) and each eluted fraction was manually collected in a 2 mL glass vial. The sequences of the peptides synthesized (both the acetylated and nonacetylated peptides) were determined by HPLC and ESI-MS analyses.

A2) Peptides of SEQ. 1 to SEQ. 25

Thus, after the peptides were synthesized, purified and examined, tests were carried out in order to determine their biological activities. Most of them also proved to have an antibacterial activity.

Furthermore, it became apparent, surprisingly and unexpectedly, that the peptides according to the invention exhibited properties which modify the microtubules of cancer cells, and in particular the peptide SEQ. 1 for which the results are described below. This peptide is a short peptide of 14 amino acids. This peptide has the following amino acid sequence: INWLKIA KKVA GML-NH$_2$ (SEQ. 1).

The peptides of sequence SEQ. 2 to SEQ. 25 are variants or homologs of the peptide of SEQ. 1. These variants differ from the peptide SEQ. 1 by virtue of one to three amino acids (absence or substitution of one or more amino acids) and/or by virtue of the absence of the —NH$_2$ group at the N-terminal end. These variants either proved to be just as effective as the peptide of SEQ. 1, or showed a slightly lower effectiveness than the peptide of SEQ. 1, but they are generally more active on types of cancer which do not respond quite as well to the peptide SEQ. 1.

B) EXPERIMENTAL TESTS

B1) Effect of the Peptide of Sequence SEQ. 1 on the Properties of Purified Microtubules (FIG. 1)

Microtubules purified from rat brain were prepared by means of an in vitro method dependent on the assembly temperature at 37° C. and disassembly temperature at 4° C. in the presence of GTP (guanosine triphosphate) described by Fellous et al. (1977) "microtubule assembly in vitro, purification of assembly-promoting factors", Eur J Biochem, 15 Aug. 1977, 15; 78(1):167-174.

The in vitro polymerization of the microtubules was monitored by measuring the changes in turbidity at 345 nm every 30 seconds during an incubation period of 15 min. The optical density measurements were carried out with a Uvicon spectrophotometer thermostated at 37° C. and equipped with an automatic loader which can receive six cuvettes.

As represented in FIG. 1, the peptide of SEQ. 1 induces a considerable increase in turbidity during the microtubule polymerization process compared with the control sample which does not comprise the peptide of SEQ. 1 and which is used as a control for the microtubule polymerization. The increase in absorbance observed in the presence of the peptide of SEQ. 1 goes hand in hand with the increase in its concentration and can reach a very high level, which can only be explained by the increase in polymerized normal microtubules alone. These data thus imply the formation of structures of abnormal microtubules or of unorganized aggregates of tubulin in the presence of the peptide of SEQ. 1. Consequently, FIG. 1 shows that the peptide SEQ. 1 has a direct action on purified microtubules and that, consequently, intracellular microtubules should constitute a target for the peptide. Moreover, this polymerization of abnormal microtubules resembles the polymerization of microtubules which takes place in the presence of a high level of an already known anticancer agent: Taxol.

B2) Action of the Peptide SEQ. 1: Similar to the Action of Taxol (FIG. 2)

Another argument which strongly suggests that the peptide of SEQ. 1 and Taxol exhibit a certain amount of similarity in their mechanism of action is demonstrated in FIG. 2.

The same type of experiment using the same technology as for B1) was carried out in order to evaluate the stability of the microtubules formed in the presence of increasing concentrations of the peptide of SEQ. 1. This stability is indicated by the inability of these microtubules to depolymerize after a treatment at 4° C. for 30 min.

Indeed, a decrease in the ability of the microtubules to depolymerize is observed in the presence of SEQ. 1 when they are subjected to the temperature of 4° C. for 30 minutes. The higher the concentration of SEQ. 1, the greater this decrease is. It becomes complete if the concentration of SEQ. 1 is very high. The microtubules formed in the presence of very high concentrations of the peptide of SEQ. 1 in fact lose their ability to depolymerize when they are subjected for 30 min to a temperature of 4° C.

The fact that the peptide of SEQ. 1 has a mechanism of action very close to that of Taxol is a definite advantage of the present invention. It should also be added that the observations made by the applicant demonstrating the irreversible effect of the peptide of SEQ. 1 on the microtubule properties give it a major advantage over other anti-microtubule peptides such as dolostatins, the effect of which on microtubules is reversible.

Assays at the cellular level confirm that the peptide of SEQ. 1 has a mechanism of action similar to that of Taxol. These assays in fact show that the peptide of SEQ. 1 abnormally and irreversibly increases the intracellular concentration of polymerized and/or aggregated tubulin, thus inducing blockage of the mitosis process.

However, the peptide of SEQ. 1 does not appear to bind to the same site on tubulin as Taxol, since several lines obtained from breast tumors which are resistant to Taxol and which have kept this property of resistance in culture. These cells in vitro have shown a high sensitivity to the peptide of SEQ. 1 and to some analogs of this peptide (cf. section B9).

Such an observation is a major one since it will be possible to envision an effective therapy using the peptides SEQ. 1 to 25 for patients who do not respond or who no longer respond to treatment with Taxol.

B3) Effect of the Peptide of SEQ. 1 on the Modification of the Organization of the Microtubule Network of Cancer Cells Via Immunofluorescent Labeling of Assembled Tubulins (FIG. 3)

In order to verify the hypothesis that the peptide of SEQ. 1 could prevent the proliferation of cancer cells by modifying the microtubule network (i.e. by having a mechanism of action close to that of the "Taxol-like mechanism"), experiments consisting of immunofluorescent labeling of the microtubule structures of cells treated or not treated with the peptide of SEQ. 1 were carried out using the method described below.

Cancer cells of various lines (A549: lung cancer; NMT1: melanoma; Panc1: pancreatic cancer) were incubated on glass slides with various concentrations of the peptide of SEQ. 1 for 4 hours at 37° C. Next, the cells were fixed with PFA, washed with PBS and incubated in a PBS buffer (phosphate buffered saline) containing 1% of BSA, 0.1% of Triton X 100 for 30 minutes at 37° C. After washing with PBS, the cells were incubated with an anti-beta tubulin monoclonal antibody overnight in a cold room. Next, the glass slides were washed with PBS and the cells were incubated with a goat anti-mouse antibody coupled to fluorescein isothiocyanate (FITC) for 60 minutes at ambient temperature. After washing with PBS, the labeled cells were visualized with a fluorescence microscope. The dapi staining technique was used to label the nuclei blue.

As represented in FIG. 3, when the lung cancer A 549 cells are treated with the peptide of SEQ. 1, even during a short period of time, there is formation of very dense polymers of tubulin which are a mixture of microtubules and of aggregates. When these cells are not treated with the peptide of SEQ. 1, the microtubule network is very organized and undisrupted. FIG. 3 also shows the effect of the peptide of SEQ. 1 on two other varieties of cancer cells, MNT-1 melanoma cells and PANC 1 pancreatic cells. When these cells are treated with the peptide SEQ. 1, their microtubule network is also modified, as shown by the significant increase in fluorescence compared with the fluorescence of the nontreated cells. However, the microtubule modification observed in the treated MNT-1 and PANC 1 cells is not as great as in the A549 cells. This can be explained by the fact that the treatment period was not sufficient or by the fact that the tubulins of the MNT-1 and PANC I lines have differences in their molecular structure compared with the tubulins of the A549 cells, and would thus be capable of inducing a reduction in their affinity for the peptide SEQ. 1.

B4) Activity of the Peptide of SEQ. 1 on Healthy Cells (FIG. 4)

The specific activity of the peptide of SEQ. 1 on cancer cells and not on healthy cells was confirmed by the experiments shown in FIG. 4. Two varieties of nontumorigenic fibroblast cells: FIBRO 1 and FIBRO 2, were brought into contact with the peptide of SEQ. 1 in order to see whether the microtubule network of healthy cells was also disrupted by the peptide. As it happens, FIG. 4 demonstrates that the human fibroblasts which represent a variety of normal cells do not respond at all to the peptide of SEQ. 1 (no modification of polymerized tubulin density), at the very least at concentrations of peptide of SEQ. 1 used for the cancer cells (15 µM). This observation represents an important advance of the present invention. Very few antitumor agents exhibit a very great difference in cytotoxicity for the cancer cells compared with the healthy cells of the host organism (i.e. very toxic for the cancer cells and weakly toxic for the healthy cells of the host).

The latter point has two important consequences: it is in fact very likely that few side effects will occur when the peptide of SEQ. 1 and analogs thereof are used as a therapeutic agent in mammals, in particular in humans.

Furthermore, it will be possible to significantly increase the efficacy of the peptide of SEQ. 1 and of analogs thereof by increasing either the dosage thereof or the treatment time thereof.

B5) Measurement of Cell Proliferation and Cell Viability (FIG. 5)

The following cell lines (table II) were analyzed in order to determine and quantify the activity of the peptide of SEQ. 1. In table II which follows, the fibroblasts M and N are not tumor cells, the lymphocytes L.1, L.3, L.4 and L.5 are leukemic, while the lymphocytes L.6 are normal lymphocytes.

Approximately 10 000 cells were seeded, in a volume of 0.2 mL per well, into 96-well microplates for 24 hours before treatment with the peptide of SEQ. 1. The cells were incubated for 48 to 72 hours at 37° C. in a $CO_2$ incubator in the presence or absence of the peptide of SEQ. 1 at various concentrations.

Following this incubation, MTT reagent or 3-(4,5-dimethyl-2-yl)-2,5-diphenyltetrazolium bromide (0.5 mg/ml in a volume of 0.1 ml) was added to each well and incubated for 2 hours at 37° C.

TABLE II

| Tissue type | Cell line | Code selected for the cell line |
|---|---|---|
| Lung cancer | A549 | G |
| Liver cancer | HepG2 | C |
| Glioblastoma | U 87-M 6 | P |
| Pancreatic cancer | MiaPaCa | S |
| Pancreatic cancer | PANC-1 | R |
| Neuroblastoma | SK N F 1 | P |
| Adrenal gland | H2.95 R | X |
| Melanoma | MNT-1 | Y |
| Chorioepithelioma | JEG | D |
| Chorioepithelioma | BEWO | E |
| Prostate cancer | DU 145 | L |
| Prostate cancer | LnCaP | K |
| Breast cancer | T 47 | B |
| Colon cancer | HT 29 | F |
| IVG fibroblasts | FIBRO 1 | M |
| N 12 fibroblasts | FIBRO 2 | N |
| Leukemic lymphocytes | HL 60 | L. 1 |
| Leukemic lymphocytes | U 937 | L. 3 |
| Leukemic lymphocytes | NB 4 | L. 4 |
| Leukemic lymphocytes | MenoMac 6 | L. 5 |
| Normal lymphocytes |  | L. 6 |

The tetrazolium ring contained by the MTT is then reduced by the succinate dehydrogenase of the live cells, to give formazan. Next, the supernatant was removed and 0.1 ml of lysis buffer (isopropanol containing 10% of triton×100 and 10% of 1N HCl) was added in order to dissolve the bluish violet formazan precipitate formed. After a few minutes, the absorbance was determined at ambient temperature using a microplate reader at a test wavelength of 562 nm. Wells not comprising peptide of SEQ. 1 were used so as to verify the viability of control cells. IC 50 (concentration of peptide of SEQ. 1 causing 50% cytotoxicity on these cell lines) values for each cell variety were evaluated by means of the ratio of the absorbance of the treated cells to the absorbance of the control cells.

Another method for measuring cell viability was used. This method consists in performing a direct visual count of the number of cells, with the assistance of a Malassez cell, under various treatment conditions. This method enables a better evaluation of the steps preceding cell death (better visibility under a microscope by direct observation of cells) than with the MTT test.

As is represented in FIG. 5 and table III, the peptide of SEQ. 1 prevents tumor cell proliferation. The higher the dose of the peptide of SEQ. 1, the greater the prevention of the cancer cell proliferation. It was observed that the doses of peptide SEQ. 1 that are toxic for the cancer cells are not toxic for normal cells, such as the normal lymphocytes or the fibroblasts. According to the applicant, the peptide SEQ. 1 decreases cancer cell proliferation probably by modifying mitotic spindle microtubule formation.

It was also observed that the sensitivity of the various varieties of tumor cells varies. Table III below proves that the IC 50 value is very low for the very sensitive tumor cells, such as the A549 cell variety (lung cancer). The IC 50 value is higher for cell varieties that are less sensitive, such as the pancreatic cells (PANC 1 cell variety) or MNT 1 human melanoma cell varieties (DU 145 cell variety) or glioblastoma cell varieties (U87-M6). In the latter case, the sensitivity depends on the time of exposure of the glioblastoma cells to the peptide of SEQ. 1. This observation suggests that the peptide of SEQ. 1 could exhibit a different efficacy and action according to the cancer cell type. A modulation of the dose or of the length of treatment can therefore be envisioned for acting effectively on certain types of cancers. The set of results in table III clearly shows that the peptide of SEQ. 1 has a very broad antitumor activity which could be greater than that of Taxol for combating various types of cancers.

Table III also shows the very low toxicity of the peptide SEQ. 1 on various types of normal cells, such as lymphocytes or fibroblasts.

This table shows that the peptide of SEQ. 1 has an activity on a large panel of cancer cells (cell viability measurement).

TABLE III

| After 48 hours of treatment with the peptide of SEQ. 1 | | |
| --- | --- | --- |
| Cell type | Cell line code | IC50 |
| A 549 (Human lung tumor) | G | 4.40 |
| COS (Monkey kidney tumor) | T | 16.48 |
| MiaPaCa (Human pancreatic tumor) | S | 23.10 |
| PANC 1 (Human pancreatic tumor) | R | 14.35 |
| H2 95R (Adrenal medullary tumor) | X | 5.40 |
| MNT-1 (Human melanoma) | Y | 8.30 |
| U87 M6 (Glioblastoma) | P | 15.26 |
| HepG2 (Hepatoma) | C | 35.60 |
| SK-N-F1 (Neuroblastoma) | O | 2.88 |
| Acute promyelocytic leukemia cell line | L.1 | 7.90 |
| Leukemia cell line | L.3 | 4.10 |
| Acute promyelocytic leukemia cell line | L.4 | 52.40 |
| Monocytic cell line | L.5 | 4.50 |
| Normal lymphocytes | L.6 | >10 |
| Fibroblasts | M | 17.80 |
| Fibroblasts | N | 22 |

| After 72 hours of treatment with the peptide of SEQ. 1 | | | |
| --- | --- | --- | --- |
| Cell type | Cell line | Cell line code | IC50 |
| Glioblastoma | U87-M6 | P | 6.00 |
| | | Fibro 1 and 2/ | >25 |

B6) Effects of the Peptide of SEQ. 1 on the Plasma Membrane Structure (FIGS. 6 and 7)

The effects of SEQ. 1 on the structure and properties of the plasma membrane were demonstrated by experiments consisting in direct observation of the treated cells under a phase contrast microscope and by experiments consisting in counting the cells which adhere and those which have lost their ability to adhere to the substrate.

Figure 1:
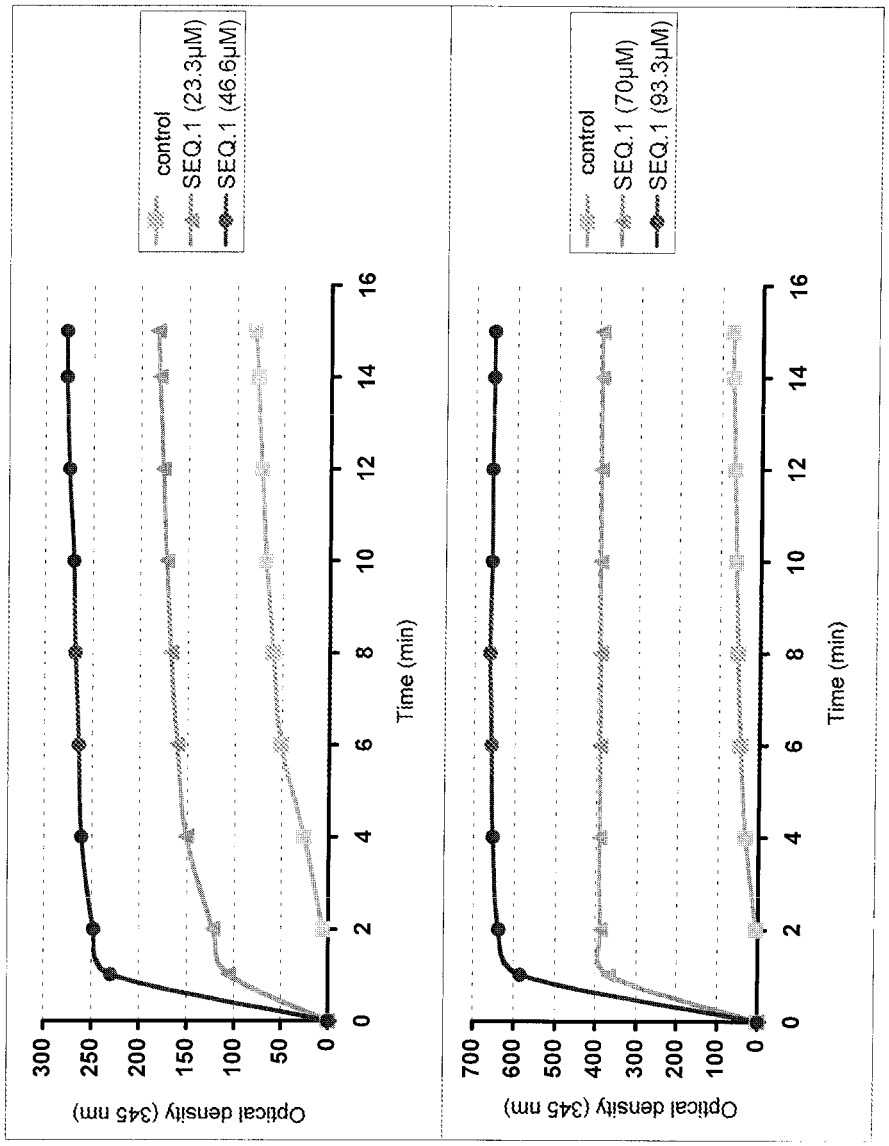
Figure 2:
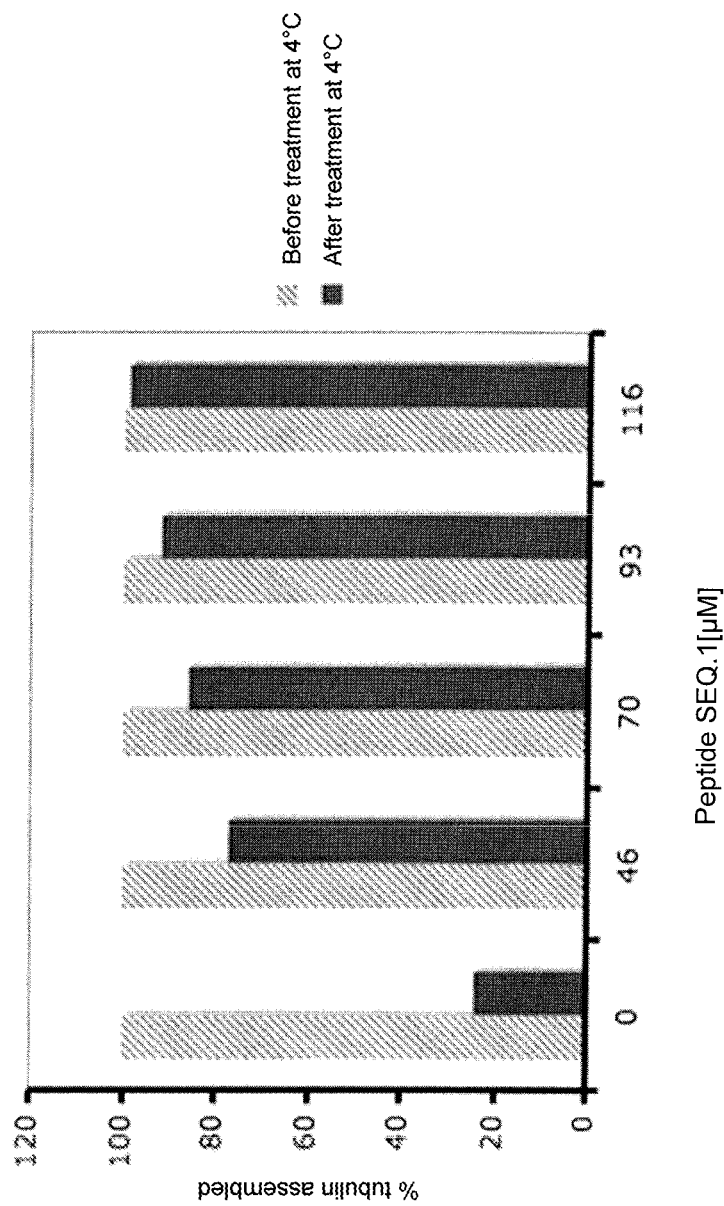
Figure 3:
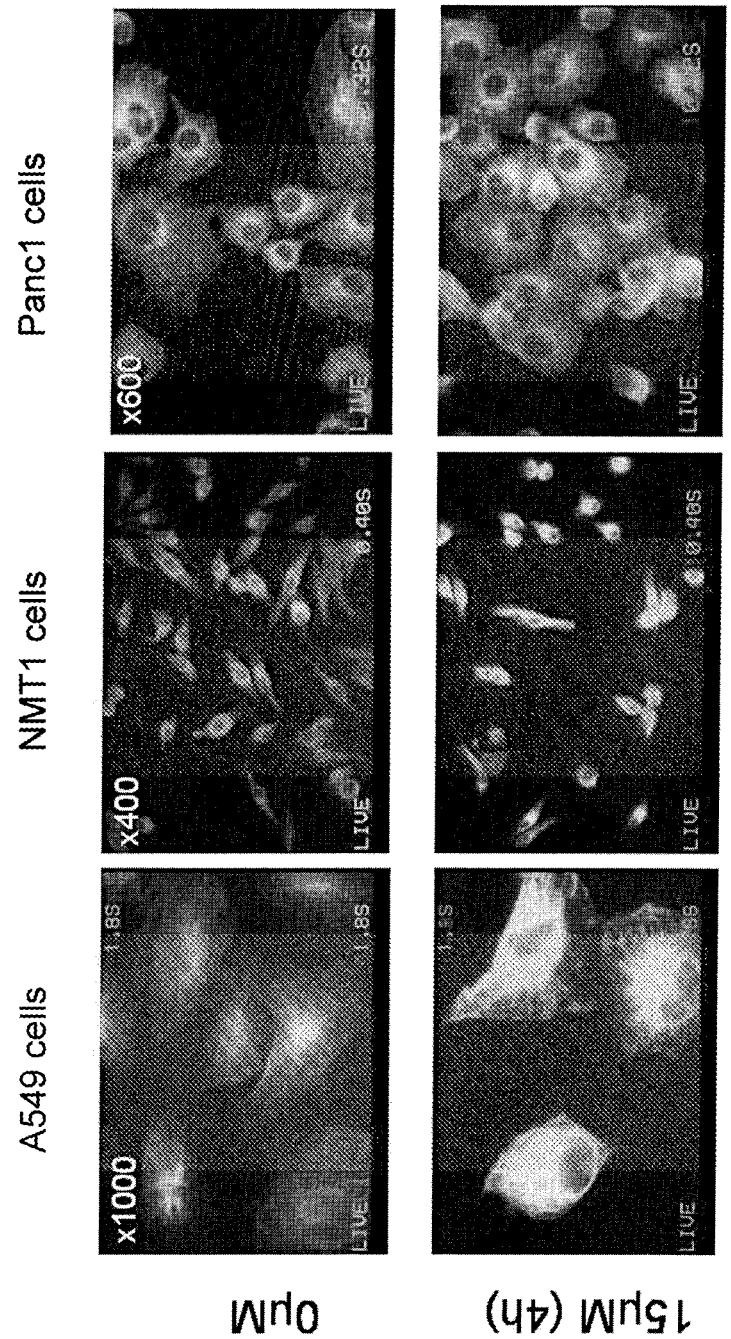
Figure 4:
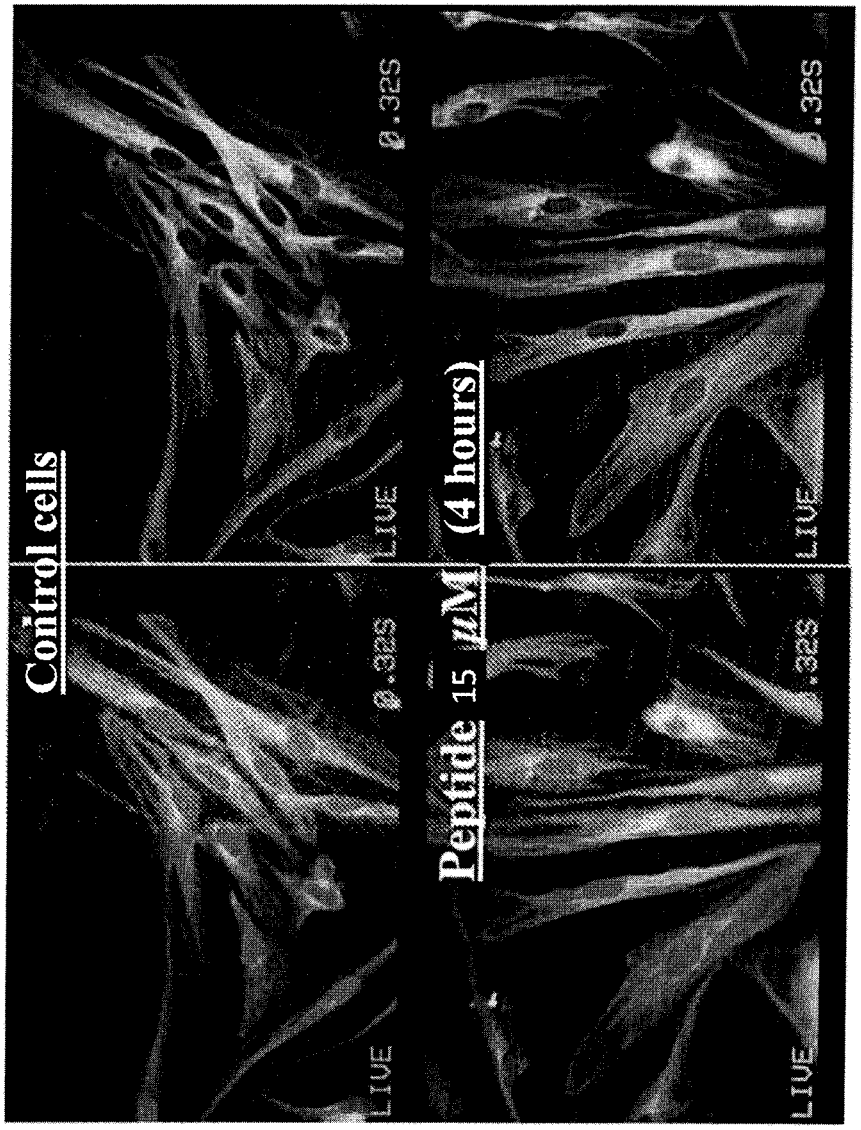
Figure 5:
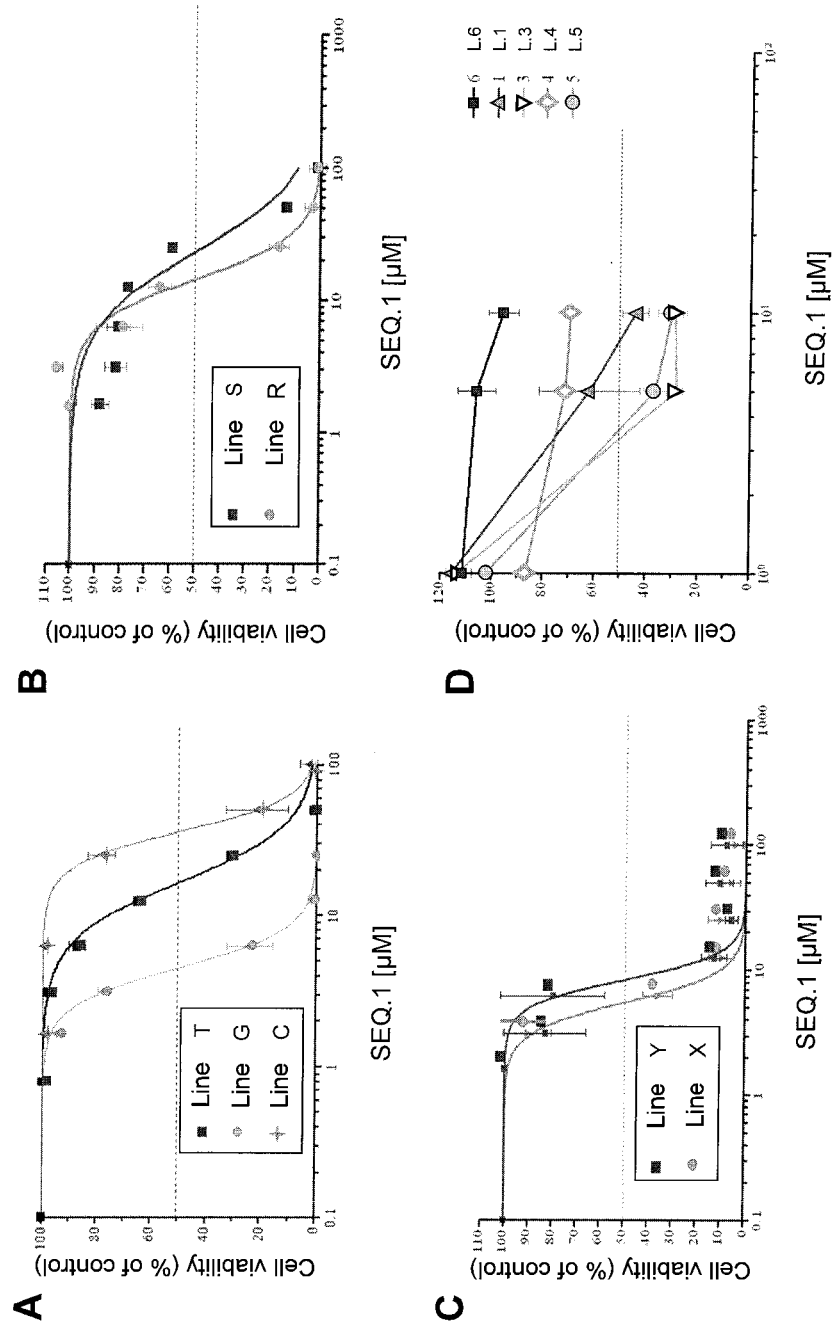
Figure 6:
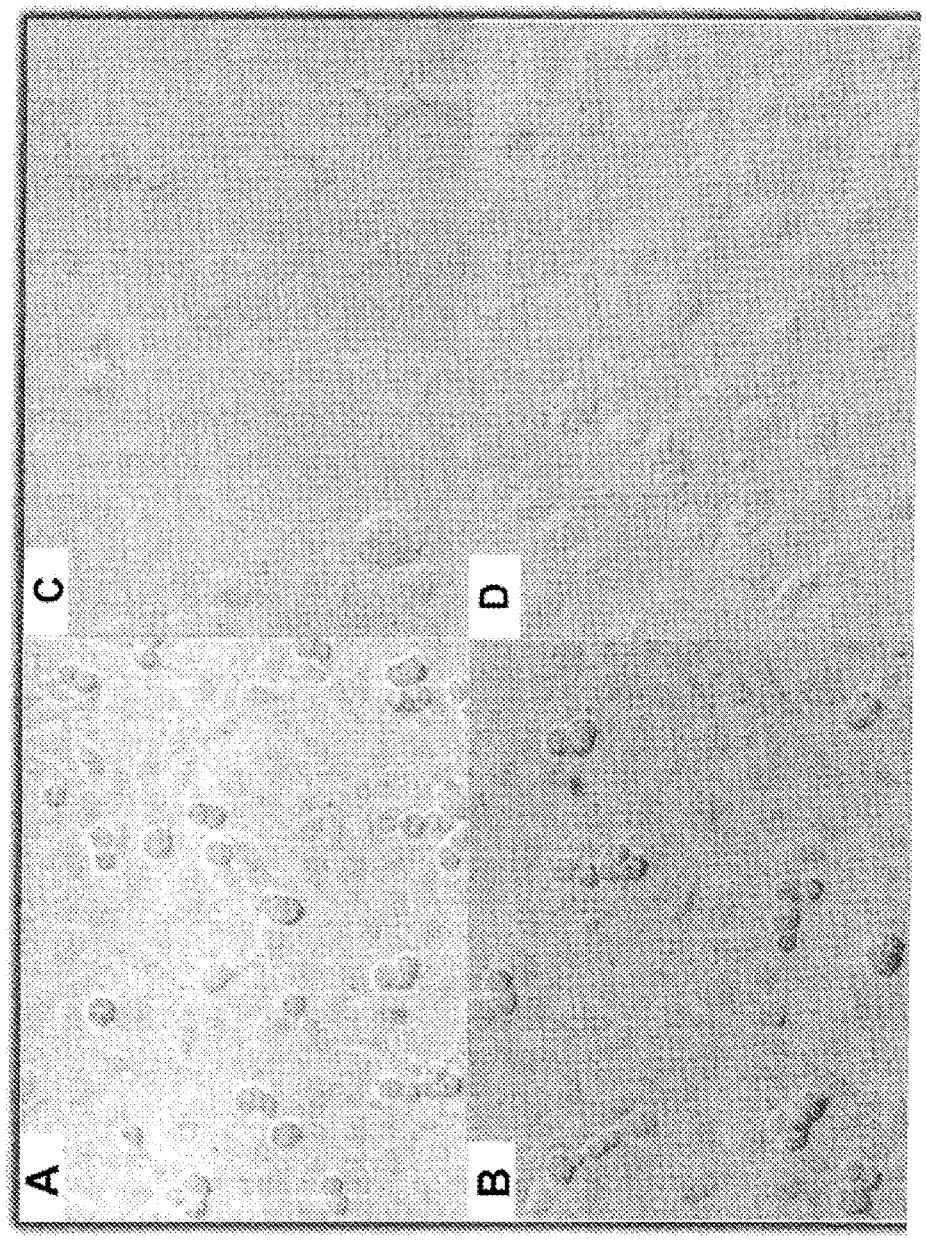
FIG. 6 shows that, in the presence of the peptide of SEQ. 1, the number of A549 tumor cells greatly decreased (after 2 and 4 hours of treatment) and that, in addition, their cell outline is greatly modified as a result of the modifications of the plasma membrane. This adds to the modifications affecting the microtubule cytoskeleton.
Figure 7:
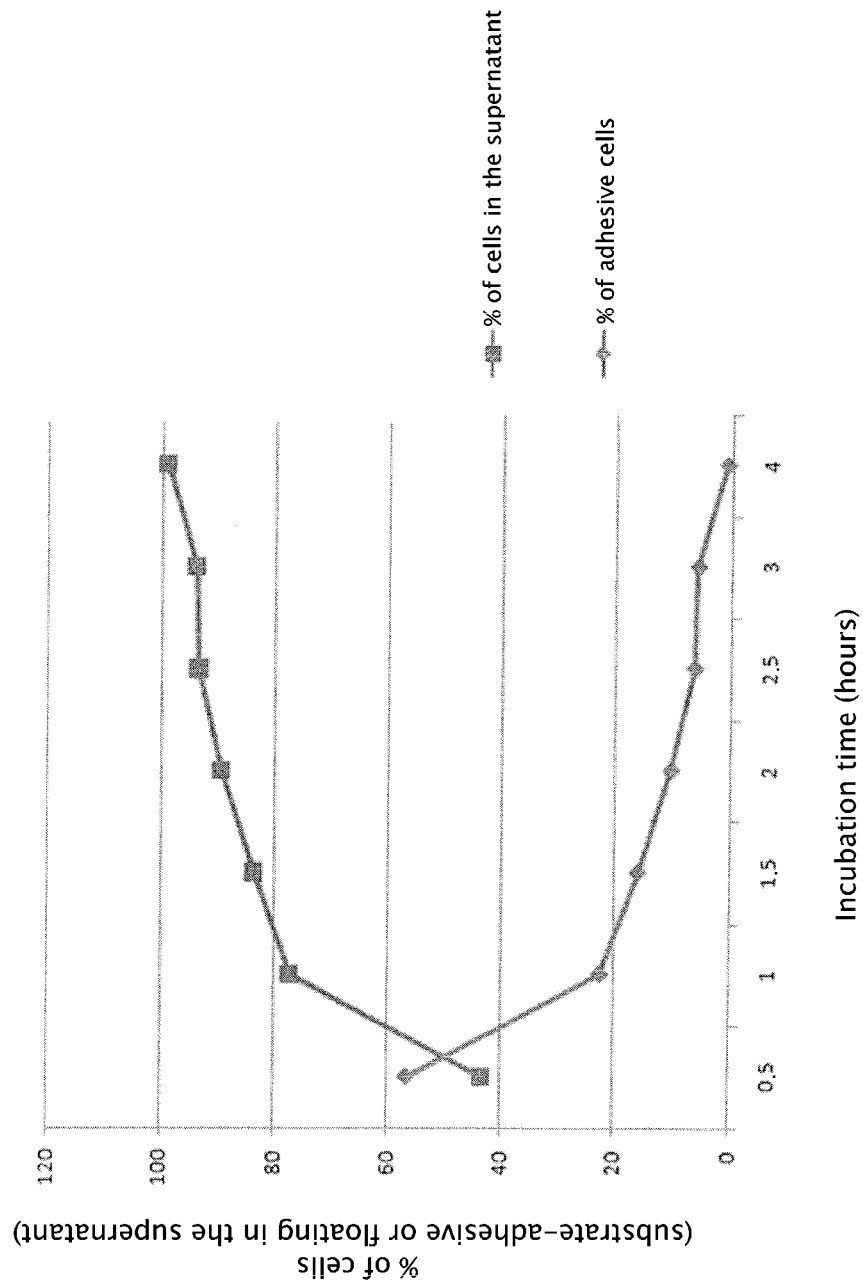
FIG. 7 shows in fact that the number of A 549 cells, which retain their substrate-adhesion properties, decreases as a function of incubation time and that, conversely, the number of A 549 cells which float in the supernatant because of a loss of adhesiveness to the substrate increases as a function of culture time.

The peptide of SEQ. 1, by virtue of its polycationic nature, modifies the properties of the plasma membranes of cancer cells rich in negatively charged phospholipids by destabilizing the structure of the lipid bilayer of these cells. This membrane destabilization leads to cell deformations by inducing either cytoplasmic extensions or deformations of the cell outline, as shown by the experiment illustrated in FIG. 6, where, in the treated cells, an abnormal cell outline with increase in cell volume is seen. The destabilization of the membranes also leads to functional changes, such as a loss of adhesion to the culture substrate, as indicated in FIG. 7.

These membrane modifications are responsible for a considerable amount of cell death. Therefore, the peptide of SEQ. 1 and certain variants exert a double, cytostatic (inhibition of mitoses) and cytotoxic (cell deaths), effect. This double effect amplifies the antitumor action of these peptides.

The peptide of SEQ. 1 and certain analogs may not modify only the membranes of cancer cells. They may modify the membranes of other cell types, such as, for example, bacterial or fungal cells.

B7) Effects of the Analogs of the Peptide of Sequence SEQ. 1

The analogs or variants of the peptide SEQ. 1 were tested on the A549 line which corresponds to a lung cancer that is still very difficult to treat. The variants tested are the following: SEQ. 3, SEQ. 4, SEQ. 7, SEQ. 9, SEQ. 18, SEQ. 19 and SEQ. 2.

The evaluation of the activity of various variants tested can be summarized as follows:

| | | |
| --- | --- | --- |
| 5 μm < IC < 10 μm | SEQ. 3, SEQ. 4, SEQ. 7, and SEQ. 9 | Very good activity close to that of the peptide SEQ. 1 |
| IC 50 about 15 μM | SEQ. 18, SEQ. 19 and SEQ. 2 | Medium activity |

In conclusion to the analysis of the activity of the variants of the peptide of SEQ. 1, it is possible to state that at least four peptides, which exhibit a modified sequence compared with that of SEQ. 1, namely the peptides of SEQ. 3, SEQ. 4, SEQ. 7 and SEQ. 9, have a cytotoxic activity which is absolutely equivalent to the peptide SEQ. 1 with respect to A 549 cells.

Another result concerns the peptide of SEQ. 7. This peptide was not only found to be active against A 549 cells, but it also exhibited a certain activity against the MNT-1 melanoma cells, with an IC 50 of between 10 and 15 μM, and also against the T47 breast cancer cells, with an IC 50 of between 10 and 15 μM.

In addition, by increasing the dosage or by increasing the treatment over time of the peptides, it will be possible to improve the efficacy of the treatment against cancer. For example, by increasing the dosage of SEQ. 1, it will be possible to obtain better results for treating moderately sensitive tumors, such as certain PANC-1 pancreatic tumors or glioblastoma.

B8) Resistance of Cancer Cells with Respect to the Peptides SEQ. 1 to 25

Finally, according to the indications of the preliminary experiments, the peptide of SEQ. 1 and analogs thereof would have the advantage of not inducing a rapid resistance process.

B9) Sensitivity of Taxol-Resistant Cells to the Peptides of Sequences SEQ. 1 and SEQ. 7

The studies were carried out on two cell lines, TX 1 and TX 2, derived from breast tumors which no longer respond to Taxol. The two lines showed very good sensitivity to at least two peptides, namely the peptide of SEQ. 1 and the peptide of SEQ. 7. More specifically, the growth inhibition results were found to be already significant after 24 H of culture in the presence of these peptides.

After 48 H of culture in the presence of the peptides, the growth inhibition evaluations are the following:

|  | IC50 in μM with peptide of SEQ. 1 | IC50 in μM with peptide of SEQ. 7 |
|---|---|---|
| TX 1 cells | 5 | 3 |
| TX 2 cells | 10 | 7 |

For the two types of resistant cells TX 1 and TX 2, the peptides SEQ. 1 and SEQ. 7 exhibit very good sensitivity, since the IC 50 index evaluated was between 3 and 7 μM.

Although the invention has been described in connection with one particular embodiment, it is quite obvious that it is in no way limited thereto and that it comprises all the technical equivalents of the means described and also the combinations thereof if said combinations fall within the context of the invention.

The invention claimed is:

1. An isolated peptide, produced by chemical synthesis, consisting of the sequence selected from the group consisting of SEQ ID NO: 2 to SEQ ID NO: 25.

2. The peptide of claim 1, wherein the peptide comprises an acetylated N-terminal residue.

3. The peptide of claim 1, consisting of the sequence selected from the group consisting of SEQ ID NO: 3 to SEQ ID NO: 25.

4. The peptide of claim 1, consisting of the sequence selected from the group consisting of SEQ ID NO: 3 to SEQ ID NO: 25.

5. The peptide of claim 1, consisting of the sequence selected from the group consisting of SEQ ID NOs: 3, 4, 7 and 9.

6. A pharmaceutical composition, comprising at least one peptide according to claim 1, and a pharmacuetically acceptable carrier.

7. The pharmaceutical composition as claimed in claim 6, wherein the composition is in the form of an aqueous suspension or solution, tablets, pills, gel capsules, capsules or powders.

8. The pharmaceutical composition as claimed in claim 6, formulated to be administered topically in the form of a cutaneous, transcutaneous or percutaneous application.

9. The pharmaceutical composition of claim 6, formulated to be administered in the form of an oral, parenteral, nasal or bronchial application.

10. A method of treating cancer in a patient, comprising administering to a patient in need thereof an effective amount of a peptide consisting of the sequence selected from the group consisting of SEQ ID NO: 2 to SEQ ID NO: 25.

11. The method of claim 10, wherein the cancer is lung cancer, breast cancer, or melanoma.

12. The method of claim 10, wherein the peptide is selected from the group consisting of SEQ ID NO: 3, SEQ ID NO: 4, SEQ ID NO: 7, and SEQ ID NO: 9.

13. The method of claim 10, wherein the cancer is taxol resistant breast cancer.

14. The method of claim 10, wherein the cancer is selected from the group consisting of breast cancer, glioblastoma, brain cancer, cervical cancer, colorectal cancer, cutaneous cancer, endometrial cancer, stomach cancer, liver cancer, gastrointestinal stromal cancer, leukemia, multiple myeloma, lymphoma, Hodgkin's disease, non-Hodgkin's lymphoma, hepatocellular carcinoma, Kaposi's sarcoma, cancer of the larynx, mesothelioma, esophageal cancer, eye cancer, osteosarcoma, ovarian cancer, pancreatic cancer, skin cancer, lung cancer, prostate cancer, rhabdomyosarcoma, kidney cancer, testicular cancer, thyroid cancer, soft tissue cancer, bladder carcinoma, myeloma, bone cancer, and plasmocytoma.

15. The method of claim 10, wherein the cancer is lung cancer, and the peptide is selected from the group consisting of SEQ ID NOs: 3, 4, 7 and 9.

16. The method of claim 10, wherein the cancer is lung cancer, breast cancer, or melanoma, and the peptide consists of the sequence selected from the group consisting of SEQ ID NOs: 3, 4, 7 and 9.

* * * * *

```
                        SEQUENCE LISTING

<160> NUMBER OF SEQ ID NOS: 30

<210> SEQ ID NO 1
<211> LENGTH: 14
<212> TYPE: PRT
<213> ORGANISM: Artificial Sequence
<220> FEATURE:
<223> OTHER INFORMATION: Synthesized

<400> SEQUENCE: 1

Ile Asn Trp Leu Lys Ile Ala Lys Lys Val Ala Gly Met Leu
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthesized

<400> SEQUENCE: 2

Ile Asn Trp Leu Lys Ile Ala Lys Lys Val Ala Gly Met Leu
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthesized

<400> SEQUENCE: 3

Ile Asn Trp Leu Ala Ile Ala Lys Lys Val Ala Gly Met Leu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthesized

<400> SEQUENCE: 4

Ile Asn Trp Leu Ala Ile Ala Ala Lys Val Ala Gly Met Leu
1               5                   10

<210> SEQ ID NO 5
<211> LENGTH: 14
<212> TYPE: PRT
```

```
<213> ORGANISM: Artificial Sequence
<220> FEATURE:
<223> OTHER INFORMATION: Synthesized

<400> SEQUENCE: 5

Ile Asn Trp Leu Lys Ile Ala Ala Ala Val Ala Gly Met Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthesized

<400> SEQUENCE: 6

Ile Asn Trp Leu Ala Ile Ala Ala Ala Val Ala Gly Met Leu
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthesized

<400> SEQUENCE: 7

Ile Asn Trp Lys Lys Ile Ala Lys Lys Val Ala Gly Met Leu
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthesized

<400> SEQUENCE: 8

Ile Asn Trp Leu Lys Ile Lys Lys Lys Val Ala Gly Met Leu
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthesized

<400> SEQUENCE: 9

Ile Asn Trp Leu Lys Ile Ala Lys Lys Val Lys Gly Met Leu
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthesized

<400> SEQUENCE: 10

Ile Asn Trp Lys Lys Ile Lys Lys Lys Val Ala Gly Met Leu
1               5                   10

<210> SEQ ID NO 11
<211> LENGTH: 14
<212> TYPE: PRT
<213> ORGANISM: Artificial Sequence
```

```
<220> FEATURE:
<223> OTHER INFORMATION: Synthesized

<400> SEQUENCE: 11

Ile Asn Trp Lys Lys Ile Lys Lys Val Lys Gly Met Leu
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthesized

<400> SEQUENCE: 12

Leu Lys Ile Ala Lys Lys Val Ala Gly Met Leu
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthesized

<400> SEQUENCE: 13

Leu Lys Ile Ala Lys Lys Val Ala Gly Met Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthesized

<400> SEQUENCE: 14

Lys Ile Ala Lys Lys Val Ala Gly Met Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthesized

<400> SEQUENCE: 15

Lys Ile Ala Lys Lys Val Ala Gly Met Leu
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthesized

<400> SEQUENCE: 16

Ile Asn Trp Leu Lys Ile Ala Lys Lys Val Ala Gly Met Leu
1               5                   10

<210> SEQ ID NO 17
<211> LENGTH: 18
<212> TYPE: PRT
<213> ORGANISM: Artificial Sequence
<220> FEATURE:
```

```
<223> OTHER INFORMATION: Synthesized

<400> SEQUENCE: 17

Phe Ile Thr Cys Ile Asn Trp Leu Lys Ile Ala Lys Lys Val Ala Gly
1               5                   10                  15
Met Leu

<210> SEQ ID NO 18
<211> LENGTH: 13
<212> TYPE: PRT
<213> ORGANISM: Artificial Sequence
<220> FEATURE:
<223> OTHER INFORMATION: Synthesized

<400> SEQUENCE: 18

Ile Asn Trp Leu Lys Ile Ala Lys Lys Val Ala Gly Met
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthesized

<400> SEQUENCE: 19

Ile Asn Trp Leu Lys Ile Ala Lys Lys Val Ala Gly
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthesized

<400> SEQUENCE: 20

Ile Asn Trp Leu Lys Ile Ala Lys Lys Val Ala
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthesized

<400> SEQUENCE: 21

Ile Asn Ala Leu Lys Ile Ala Lys Lys Val Ala Gly Met Leu
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthesized

<400> SEQUENCE: 22

Ile Asn Ala Leu Lys Ile Ala Lys Lys Val Ala Gly Met Leu
1               5                   10

<210> SEQ ID NO 23
<211> LENGTH: 14
<212> TYPE: PRT
<213> ORGANISM: Artificial Sequence
```

```
<220> FEATURE:
<223> OTHER INFORMATION: Synthesized

<400> SEQUENCE: 23

Ile Asn Lys Leu Lys Ile Ala Lys Lys Val Ala Gly Met Leu
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthesized

<400> SEQUENCE: 24

Ile Asn Lys Leu Lys Ile Ala Lys Lys Val Ala Gly Met Leu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthesized

<400> SEQUENCE: 25

Lys Leu Lys Ile Ala Lys Lys Val Ala Gly Met Leu
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Synthesized

<400> SEQUENCE: 26

Glu Ala Arg Pro Ala Leu Leu Thr Ser Arg Leu Arg Phe Ile Pro Lys
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthesized

<400> SEQUENCE: 27

Asp Gly Leu Arg Pro Ile Val Asn Met Asp Tyr Val Val Gly Ala Arg
1               5                   10                  15

<210> SEQ ID NO 28
<211> LENGTH: 18
<212> TYPE: PRT
<213> ORGANISM: Artificial Sequence
<220> FEATURE:
<223> OTHER INFORMATION: Synthesized

<400> SEQUENCE: 28

Gly Val Pro Glu Tyr Gly Cys Val Val Asn Leu Arg Lys Thr Val Val
1               5                   10                  15

Asn Phe

<210> SEQ ID NO 29
<211> LENGTH: 10
<212> TYPE: PRT
```

```
<213> ORGANISM: Artificial Sequence
<220> FEATURE:
<223> OTHER INFORMATION: Synthesized

<400> SEQUENCE: 29

Ile Leu Ala Lys Phe Leu His Val Val Leu
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthesized

<400> SEQUENCE: 30

Glu Leu Leu Arg Ser Phe Phe Tyr Val
1               5
```